United States Patent [19]

Barbara et al.

[11] Patent Number: 5,507,302
[45] Date of Patent: Apr. 16, 1996

[54] DEVICE FOR MEASURING THE DEGREE OF AXIAL RIGIDITY OF THE PENIS

[76] Inventors: Mariano R. Barbara, Mirador Bahia 2, La Bona Nova, 07012 Palma de Mallorca; Juan A. M. Y. Garcia de la Serrana, Plaza Profesor Lopez Ibor 10, 46015 Valencia, both of Spain

[21] Appl. No.: 321,731

[22] Filed: Oct. 12, 1994

[30] Foreign Application Priority Data

Oct. 14, 1993 [ES] Spain ..................................... 9302162

[51] Int. Cl.$^6$ ..................................... A61B 5/10
[52] U.S. Cl. ..................................... 128/774
[58] Field of Search ..................................... 128/736, 740, 128/744, 774; 73/849, 862.391, 862.392, 862.451, 862.473

[56] References Cited

U.S. PATENT DOCUMENTS

| | | | |
|---|---|---|---|
| 3,680,386 | 8/1972 | Cannon | 128/774 |
| 4,103,678 | 8/1978 | Karacan et al. | 128/774 |
| 4,144,877 | 3/1979 | Frei et al. | 128/774 |
| 4,503,865 | 3/1985 | Shishido | 128/774 |
| 4,771,791 | 9/1988 | Kubouchi | 128/736 |

*Primary Examiner*—Max Hindenburg
*Attorney, Agent, or Firm*—Ostrolenk, Faber, Gerb & Soffen

[57] ABSTRACT

Device for measuring the degree of axial rigidity of the penis, which includes a deformable support surface (1); an electronic pressure sensor (2); an intermediate pressure transmission element (3) that reliably transmits the intensity and direction of the force applied to the membrane (1); a temperature reading sensor (12) located on the support surface (1); a microprocessor (9) responsible for determining any variation in the magnitude of the force transmitted by the intermediate body (3); and a memory (10) that stores data on pressure, temperature, date and time.

16 Claims, 4 Drawing Sheets

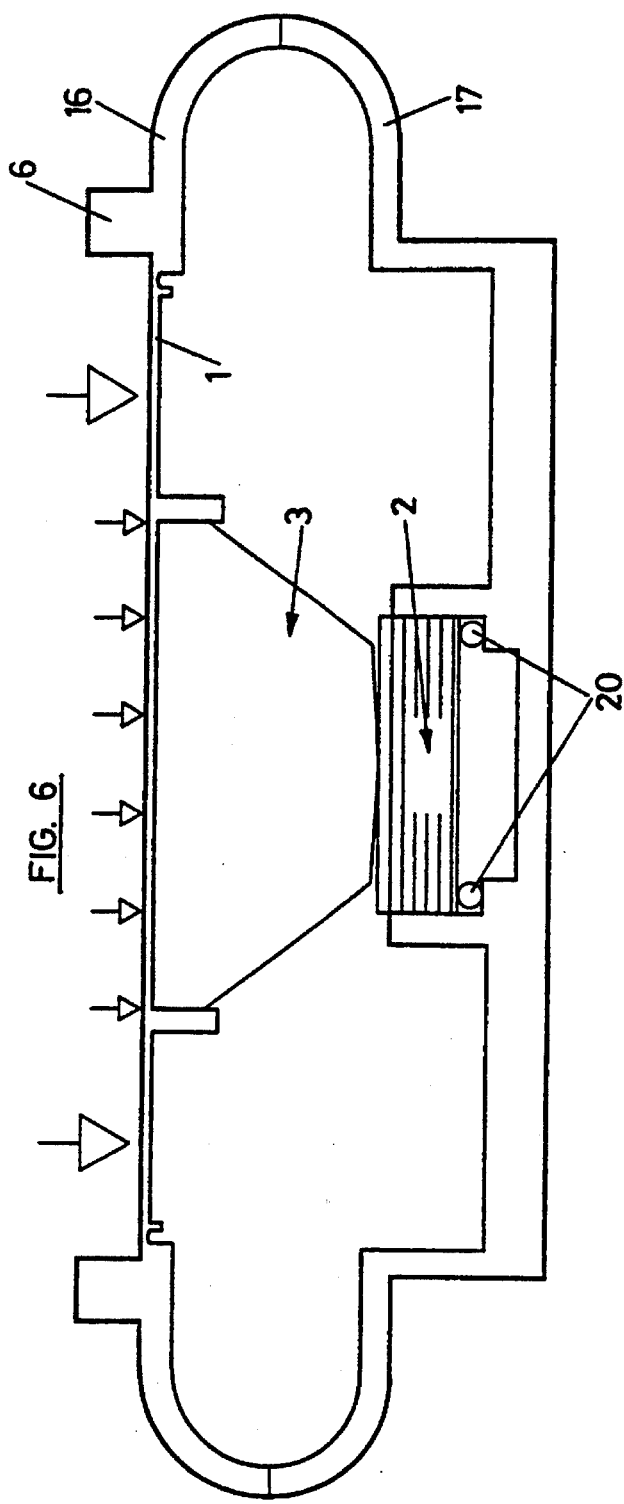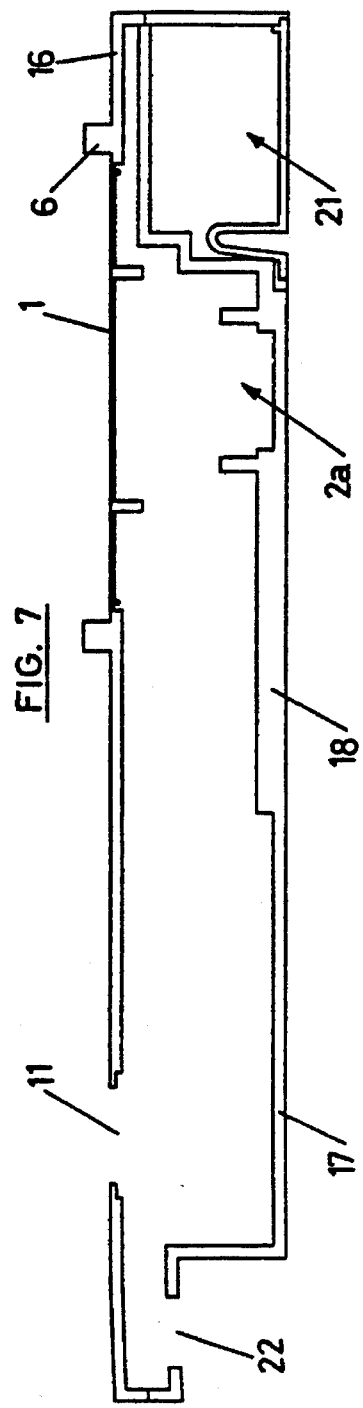

DEVICE FOR MEASURING THE DEGREE OF AXIAL RIGIDITY OF THE PENIS

BACKGROUND OF THE INVENTION

The present invention concerns a device for measuring the axial rigidity of the penis, having an electronic design, with which the necessary information can be obtained for studying possible changes or illnesses.

In 1975, and even earlier, some specialists started to use the concept of "rigidity" when they were assessing male impotence, with terms as ambiguous as: "good; average; sufficient or insufficient; short or long; etc."

The need for a parameter that would determine the quality of the erection started to be defined in 1982, as a consequence of the discovery by Dr Virag that an injection of papaverine provoked a relaxation of the arteriolar and trabecular smooth muscle of the cavernous body, causing a rigid erection in the penis. Between 1985/1986 apparatus such as the ART 1000 (USA) appeared, which allowed detection of episodes of tumescence and pseudo-rigidity during sleep in the base and at the tip of the penis, and subsequently the Rigiscan (USA), which allowed measurements of these parameters to be made in a much more precise way from the point of view of determining the quality of erection.

Nevertheless, none of them allowed the degree of axial rigidity at any moment to be evaluated; giving the circumstance that individuals with good rigidity in the base and at the tip of the penis could not maintain satisfactory sexual relations as a consequence of lack of axial rigidity for penetration.

In 1989 Dr Rosselló Barbará de España created and patented the first mechanical device for measuring the degree of rigidity of the penis in the axial direction (Utility model U8903604, submitted on 20 Nov. 1989), which allows measurement to be made of the force created by the penis in a state of erection for a perfect sexual relation.

This first device showed with practice that although it allows us to determine the maximum force of the penis during an erection, it does not allow us to determine when it undergoes an incurvation as a consequence of any of the illnesses that might be present, and which prevent proper penetration.

SUMMARY OF THE INVENTION

The object of the present invention is a totally electronic device with which we can determine two fundamental parameters from the andrological point of view, which are:

a) The maximum moment of axial force starting from which the penis changes its angle.

b) The arterial pressure existing in the cavernous bodies at the moment in which the maximum axial stress is being made.

The invention's device allows the parameters stated above to be determined by means of a portable microprocessing system with capacity for storing data from a range of measurements made with it, and which can later be treated with a statistical program by means of a PC or similar.

The invention's device is based on the determination of the linear force exerted by the penis on a deformable membrane, which acts on an electronic sensor producing an electrical voltage that can be digitalized for its interpretation by a microprocessor.

The invention's device consists of: a deformable axial support surface; an electronic pressure sensor that detects the pressure exerted on the membrane and converts it into an electrical voltage; an intermediate element for pressure transmission fitted between the membrane and the sensor, capable of reliably transmitting the intensity and direction of the force applied on the membrane; a temperature reading sensor located on the support surface; a microprocessor responsible for determining any variation in the magnitude of the force transmitted by the intermediate body, following an internal algorithm; and an internally fed memory with capacity for storing data on pressure, temperature, date and time without losing the data even when the equipment has no power, this memory being responsible for transmitting all the data to a computer for being processed and treated by a computer program.

The characteristics of the invention's device, as included in the patent claims, are stated below in greater detail with the aid of the attached drawings, in which are shown a nonrestrictive embodiment of the invention.

In the diagrams:

FIG. 6 is a schematic transverse cross-section of the device, taken along the line VI—VI of FIG. 5.

FIG. 7 is a schematic transverse cross-section of the device, taken along the line VII—VII of FIG. 5.

DETAILED DESCRIPTION OF THE PREFERRED EMBODIMENTS

Figure 1:
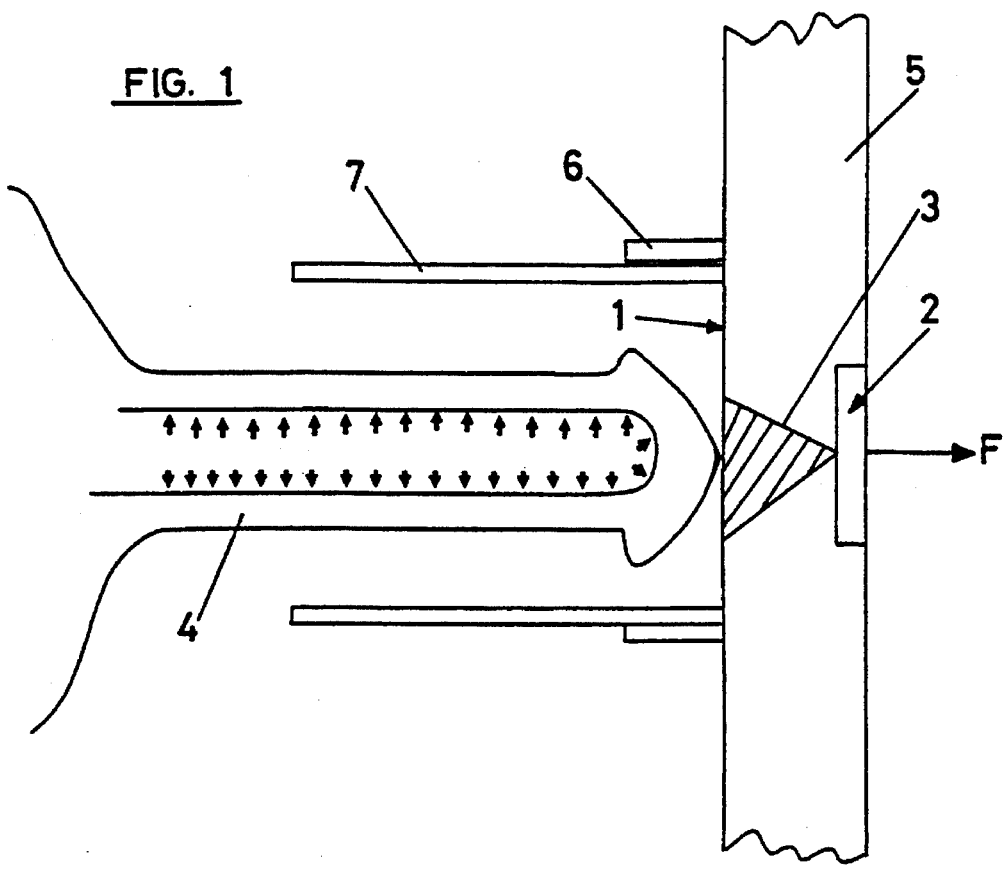
FIG. 1 is a schematic cross-section of a device designed according to the invention, in the phase of measuring the rigidity of the penis.
Figure 2:
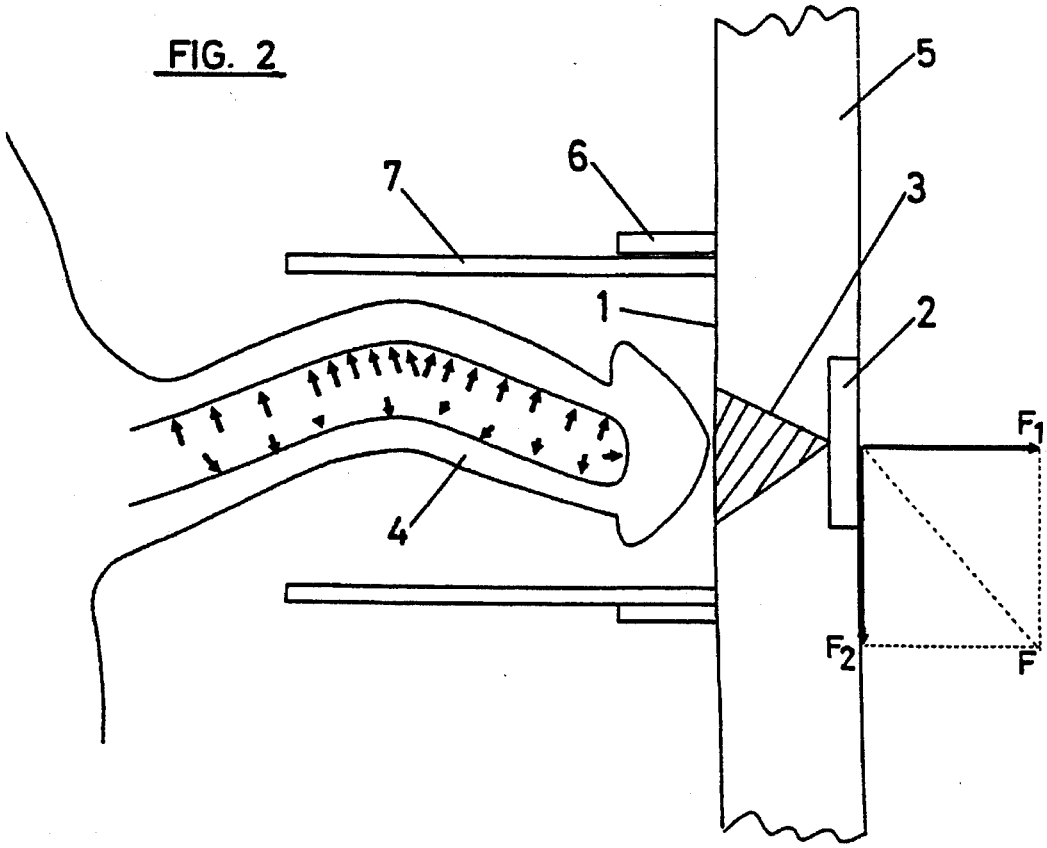
FIG. 2 is a cross-section similar to that of FIG. 1, where the penis is shown with a different degree of rigidity.

As can be appreciated from FIGS. 1 and 2, the invention's device consists of a deformable support surface, referenced with number 1, an electronic pressure sensor 2 and an intermediate pressure transmission element 3.

The deformable surface 1 will preferably consist of a membrane on which will rest the rigid penis that it is wished to measure. The intermediate pressure transmission element 3 is fitted between the membrane 1 and the sensor 2 and is designed in such a way that it can reliably transmit the intensity and direction of the force exerted on the membrane 1 by the penis 4. This intermediate element can be made from a piece of silicone, with a conical or truncated conical shape, on whose vertex or smaller base rests the pressure detector 2, and on whose larger base in turn rests the deformable membrane 1.

The electronic element can consist of an integrated microceramic. The entire unit described will be fitted inside a housing 5 which will have a hoop 6 around the membrane 1 for securing a directioning cup 7.

With the stated design, when the penis 4 rests in a state of maximum axial rigidity, the force exerted on the deformable membrane 1 is entirely transmitted via the intermediate element 3 to the electronic sensor 2. The force F transmitted to this sensor will be transformed into a voltage that can be digitalized for its interpretation by the microprocessor, as shall be explained further below. While the normal direction of application of the force F to the membrane 1 is maintained, the system is sampling the data at the rate of 400 times a second. At the moment in which the magnitude of the force changes, the system ceases taking data and automatically stores the latest data read in an EEPROM type memory. The day, date, hour and minute on which this reading was obtained are simultaneously stored in the memory. This data is recorded on the basis of a real-time clock built into the system. At the same time as the latest value read is stored in the memory, it is represented in an alphanumeric display incorporated into the equipment, where it is retained for a certain length of time for convenience of use at the clinical level.

The variation in the magnitude of the force F transmitted to the electronic sensor 2 can, as is shown in FIG. 2, be due to a variation in the direction of application of the force by the penis 4, due for example to a variation in the state of its axial rigidity. In the situation shown in FIG. 2 the force F applied to the deformable membrane 1 breaks down into a normal force $F_1$ and a tangential force $F_2$ causing the system to cease taking data, as has been explained above.

Figure 3:
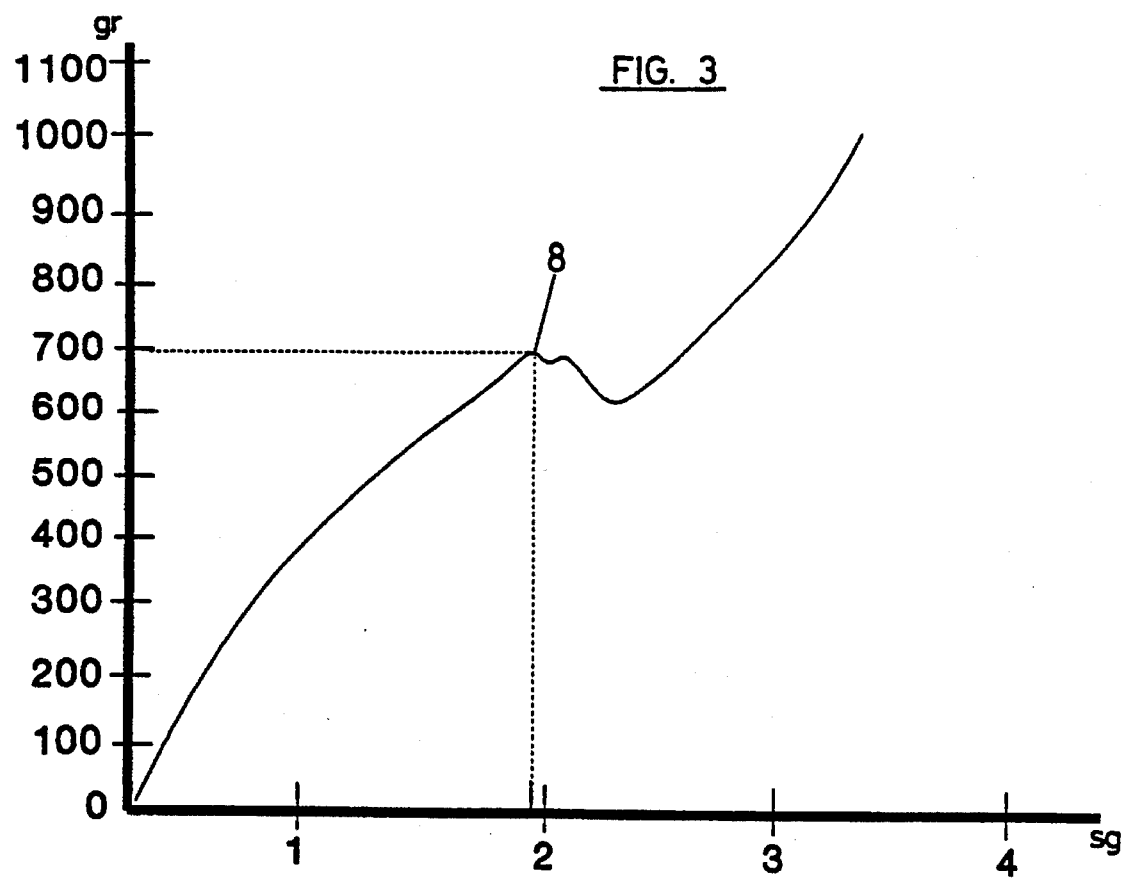
FIG. 3 is a graph representing the curve corresponding to the pressure exerted on the deformable membrane.

The graph of FIG. 3 shows how the microprocessor determines the point of inflection due to the measurement made in the situation represented in FIG. 2. In the graph of FIG. 3, the pressures are measured along the ordinate and the time along the abscissa. When a pressure starts to be exerted on the membrane 1 the electronic sensor 2 produces an equivalent and increasing electrical voltage in line with the pressure, which is monitored 400 times a second by the microprocessor. At the moment in which this pressure drops by the slightest amount, corresponding to the point of inflection 8, the microprocessor files the latest and largest magnitude value read in the memory, as well as the time at which it took place.

Figure 4:
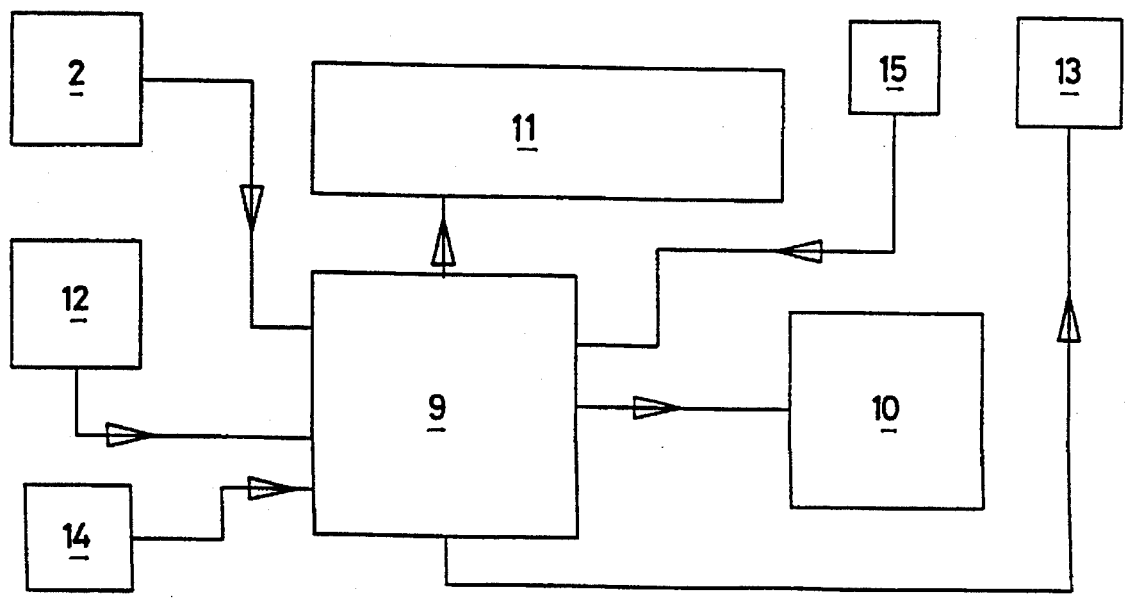
FIG. 4 shows a block diagram of an electronic circuit in accordance with the invention for the device of FIG. 1.

FIG. 4 represents a block diagram of the electronic circuit for the invention's device, consisting fundamentally of a microprocessor 9, an EEPROM memory 10, a display 11, a temperature sensor 12, the pressure sensor 2, a communication connector 13 with a PC computer system, a starter push-button 14 and a push-button 15 for storing data in the memory 10. The microprocessor 9 processes the data obtained from the pressure sensor 4 and the temperature sensor 12, and stores them in the memory 10. The starter push-button 14 for data taking and the push-button 15 for storing the data in the memory 10 show them in an alphanumeric display 11, of 2×18 characters, for example.

Figure 5:
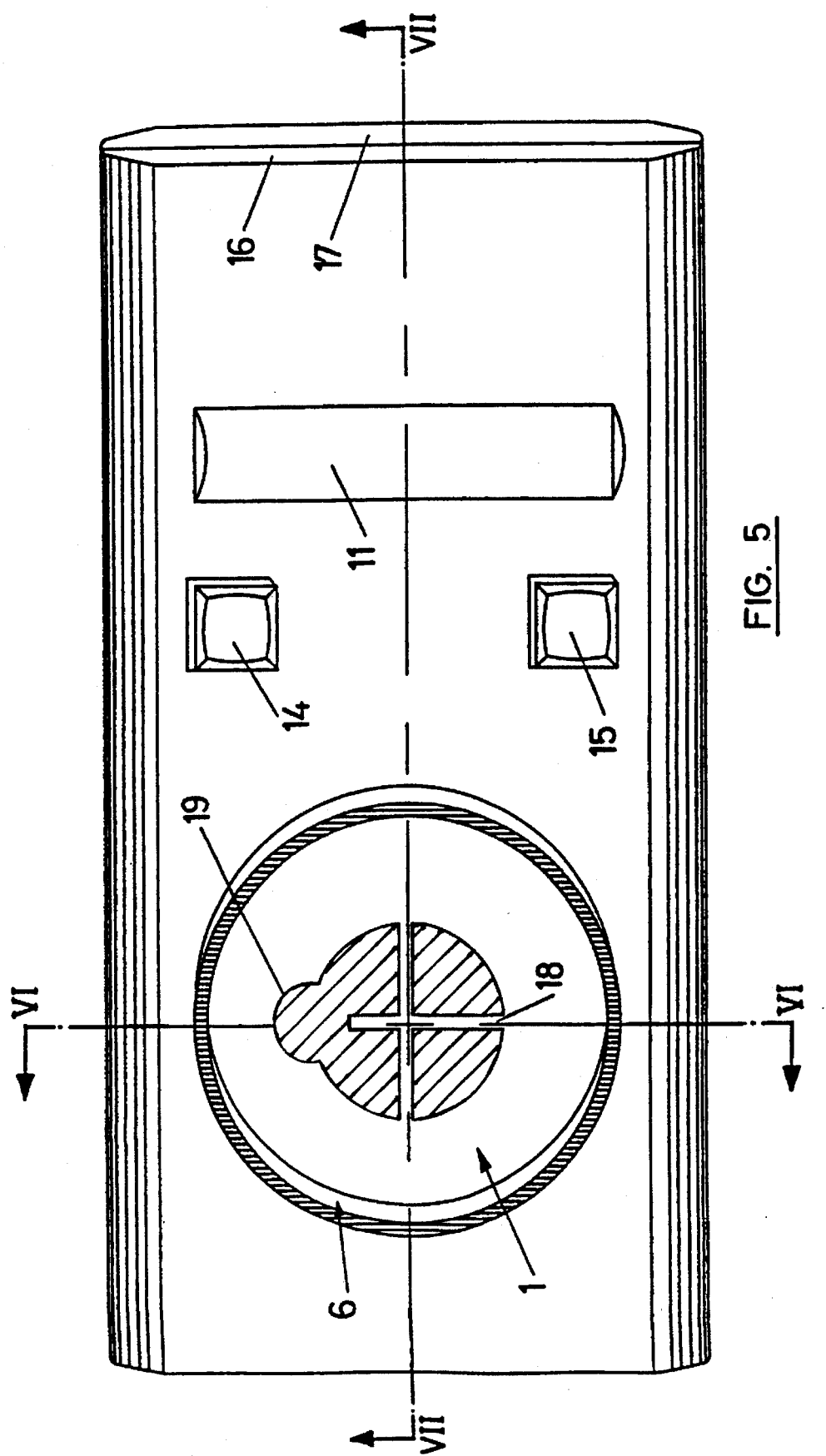
FIG. 5 shows a perspective view of one embodiment of housing for a device in accordance with the invention.

FIG. 5 shows a possible configuration of the housing in which the different components of the invention's device are contained. This housing can be made up of the bodies 16 and 17 which can be coupled and secured together. The housing includes a zone, for example, with a circular outline, which is occupied by the deformable membrane 1, surrounded by the hoop 6, which will serve for securing the directioning cup 7, FIGS. 1 and 2. Beneath the membrane will be located the intermediate pressure transmission element and the electronic sensor, whose position can be ensured by means, for example, of an internal anti-torsion spider 18. Provided on the surface of the deformable membrane 1 is a temperature sensor 19, such as of the high-sensitivity thermistor type, encapsulated in a crystal and in turn introduced into a capsule of gold filled with silicone oil and which will remain in contact with the glans in order to measure its temperature.

The housing is also provided with the corresponding window for the display 11, where the inflection force in grams and the temperature in degrees centigrade will appear. Alongside this window are located the start push-button 14 and the data storage push-button 15.

FIG. 6 shows the bodies 16 and 17 making up the housing, the deformable membrane 1, the intermediate pressure transmission element 3, with a truncated conical shape, and the electronic pressure sensor 2 which rests on an expansion compensation torus 20.

Finally, in FIG. 7, besides the half-bodies 16 and 17 making up the housing, the space 2a for location of the electronic pressure sensor 2, the deformable membrane 1, the gap 21 intended for location of the power supply source, the display window 11, the securing hoop 6 for the directioning cup, the anti-torsion spider 18 for the electronic pressure sensor 2, and the opening 22 for the data output connector to the PC can all also be appreciated.

This sensor can consist of a ceramic integrated piezoresistive cell in a double Wheatstone bridge compensated in temperature and current, which supplies information on the pressure with which the membrane 1 is acted upon to an instrumentation operational amplifier, which in turn transfers the analog information to an analog-digital converter supplying one of the channels of the microprocessor 9.

On the other hand, the differences in resistance on the basis of the temperature detected by the sensor 19 are sent to the programmable amplifier channel of the microprocessor 9.

A real-time calendar clock supplies another of the input channels of the microprocessor 9. Three of the input/output channels of the microprocessor are responsible for guarding the information in the memory 10. Eight output channels feed the display 11, responsible for visually displaying the data. Another two of the input/output channels are used for the communications protocol between the microprocessor 9 and the computer program used by the PC or similar, in order to display the statistical data on pressures and temperatures on screen.

The process of taking data and sealing the memory is initiated by means of the switches 14 and 15, once the data have been filed.

Although the present invention has been described in relation to particular embodiment(s) thereof, many other variations and modifications and other uses will become apparent to those skilled in the art. It is preferred, therefore, that the present invention be limited by the specific disclosure herein, but only by the appended claims.

We claim:

1. A device for measuring the degree of axial rigidity of a penis, comprising:

pressure responsive means placed so as to be engageable by the penis being applied axially thereto and responsive to pressure exerted on the pressure responsive means by the penis for generating an electrical signal, the pressure exerted by the penis being a function of the axial rigidity of the penis; and means responsive to the electrical signal for determining the pressure exerted by the penis on the pressure responsive means.

2. A device for measuring the degree of axial rigidity of a penis, comprising:

pressure responsive means placed so as to be engageable by the penis being axially applied thereto and responsive to pressure exerted on the pressure responsive means by the penis for generating an electrical signal in proportion to the magnitude of the pressure, the pressure exerted by the penis, changing when the axial rigidity of the penis changes; and means responsive to the electrical signal for determining a change in the pressure exerted by the penis on the pressure responsive means and for determining the magnitude of the pressure being exerted by the penis when the change occurs.

3. A device according to claim 2, wherein the pressure responsive means includes a deformable member, the deformable member being engageable by the penis and deformable in response to pressure exerted thereon by the penis.

4. A device according to claim 3, wherein the pressure responsive means includes an electronic pressure sensor for converting pressure to an electrical signal and an intermediate pressure transmission member responsive to deformation of the deformable member for applying pressure to the electronic sensor.

5. A device according to claim 4, wherein the electronic pressure sensor comprises an integrated microceramic.

6. A device according to claim 4, wherein the intermediate pressure transmission member comprises a silicone body having first and second opposed ends, the first end being in an engagement with the deformable member and the second end being in an engagement with the electronic pressure sensor.

7. A device according to claim 6, wherein the first end is larger than the second end.

8. A device according to claim 7, wherein the intermediate pressure transmission element is conically shaped.

9. A device according to claim 7, wherein the intermediate pressure element is frusto conically shaped.

10. A device according to claim 7, wherein the deformable member comprises a deformable membrane.

11. A device according to claim 10, wherein the pressure determining means includes a microprocessor.

12. A device according to claim 11, wherein the microprocessor determines the magnitude of the pressure in real time.

13. A device according to claim 12, further including means for measuring the temperature of the penis.

14. A device according to claim 13, further including means for determining the date and time the magnitude of the pressure is determined.

15. A device according to claim 13, further including storage means for storing the magnitude of pressure determined by the pressure determining means, the temperature determined by the temperature measuring means and the date and time determined by the date and time determining means.

16. A device according to claim 14, wherein the storage means is a nonvolatile storage means.

\* \* \* \* \*